United States Patent [19]

Kollonitsch

[11] Patent Number: 5,030,645

[45] Date of Patent: Jul. 9, 1991

[54] METHOD OF TREATING ASTHMA USING (S)-α-FLUOROMETHYL-HISTIDINE AND ESTERS THEREOF

[75] Inventor: Janos Kollonitsch, Westfield, N.J.

[73] Assignee: Merck & Co., Inc., Rahway, N.J.

[21] Appl. No.: 597,653

[22] Filed: Oct. 15, 1990

[51] Int. Cl.$^5$ ............................................. A61K 31/415
[52] U.S. Cl. ................................................ 514/396
[58] Field of Search .......................................... 514/396

[56] References Cited

U.S. PATENT DOCUMENTS

| | | | |
|---|---|---|---|
| 4,325,961 | 4/1982 | Kollonitsch et al. | 424/273 |
| 4,447,443 | 5/1984 | Goldberg | 424/273 |
| 4,522,823 | 6/1985 | Hanson | 424/273 |

OTHER PUBLICATIONS

J. Allergy Clin. Immunol. 74, 49 (1984).
Agricl. Biol. Chem. 52 891-3 (1988).
Agric. Biol. Chem. 52(6), 1607-1608 (1988).
Immunology 65 433-36 (1988).

*Primary Examiner*—Sidney J. Friedman
*Attorney, Agent, or Firm*—Raymond M. Speer; Hesna J. Pfeiffer

[57] ABSTRACT

(S)-α-fluoromethylhistidine, a potent, selective, mechanism-based inhibitor of mammalian histidine carboxylase, the enzyme responsible for biosynthesis of histamine in mammals, is useful in the treatment of asthma.

5 Claims, 3 Drawing Sheets

FIG-1 EFFECT OF MK453 (30mg/kg) ON ANTIGEN-INDUCED BRONCHOCONSTRICTION IN SHEEP

FIG-2 SHEEP MODEL OF ASTHMA (AEROSOL)

METHOD OF TREATING ASTHMA USING (S)-α-FLUOROMETHYL-HISTIDINE AND ESTERS THEREOF

BACKGROUND OF THE INVENTION

1. Field of the Invention

The present invention is in the field of methods of treating asthma. And more particularly, the present invention is in the field of treating asthma with pharmaceutical compounds which prevent or inhibit the basic progress of the disease, as opposed to methods of treatment which are merely palliative.

Bronchial asthma can occur secondarily to a variety of stimuli. The underlying mechanisms are unknown, but inherited or acquired imbalance of adrenergic and cholinergic control of airways diameter has been implicated. Persons manifesting such imbalance have hyperreactive bronchi and, even without symptoms, bronchoconstriction may be present. Overt asthma attacks may occur when such persons are subjected to various stresses, such as viral respiratory infection, exercise, emotional upset, nonspecific factors, e.g., changes in barometric pressure or temperature, inhalation of cold air or irritants, e.g., gasoline fumes, fresh paint and noxious odors, or cigarette smoke, exposure to specific allergens, and ingestion of aspirin or sulfites in sensitive individuals. Psychologic factors may aggravate an asthmatic attack but are not assigned a primary etiologic role.

Asthmatic attacks are characterized by narrowing of large and small airways due to spasm of bronchial smooth muscle, edema and inflammation of the bronchial mucosa, and production of tenacious mucus. The role of inflammation in the perpetuation of the abnormal airway responses (late-phase reaction) is only now being appreciated.

Mechanisms underlying bronchoconstriction are not well defined. However, an imbalance between β-adrenergic and cholinergic control of airways diameter has been proposed. In turn, the observed abnormalities in adrenergic and cholinergic functions in asthma appear to be controlled by the cyclic 3',5'-adenosine monophosphate (cyclic AMP or cAMP)-cyclic 3',5'-guanosine monophosphate (cyclic GMP or cGMP) systems within various tissues, e.g., mast cells, smooth muscle, and mucus-secreting cells. The intracellular concentration of cAMP is a principal determinant of both smooth muscle relaxation and inhibition of IgE-induced release of several mediators, which cause bronchoconstriction either directly or by cholinergic reflex action and increases exocrine section.

Antigen challenged allergic sheep are a standard animal model for human asthma, having the capability to measure the immediate bronchoconstriction and the important late phase response. Surprisingly, (S)-α-fluoromethylhistidine, in this model, dosed intravenously or by inhaled aerosol, virtually eliminated the late phase response. Since commonly used antiasthma drugs are active in this model, (S)-α-fluoromethylhistidine is expected to have antiasthma activity in man.

2. Brief Description of the Prior Art

Drug treatment for asthma includes oral phosphodiesterase inhibitors, oral and inhaled β-adrenergic agonists, oral and inhaled steroids, and inhaled inhibitors of mediator release.

SUMMARY OF THE INVENTION

Figure 1:
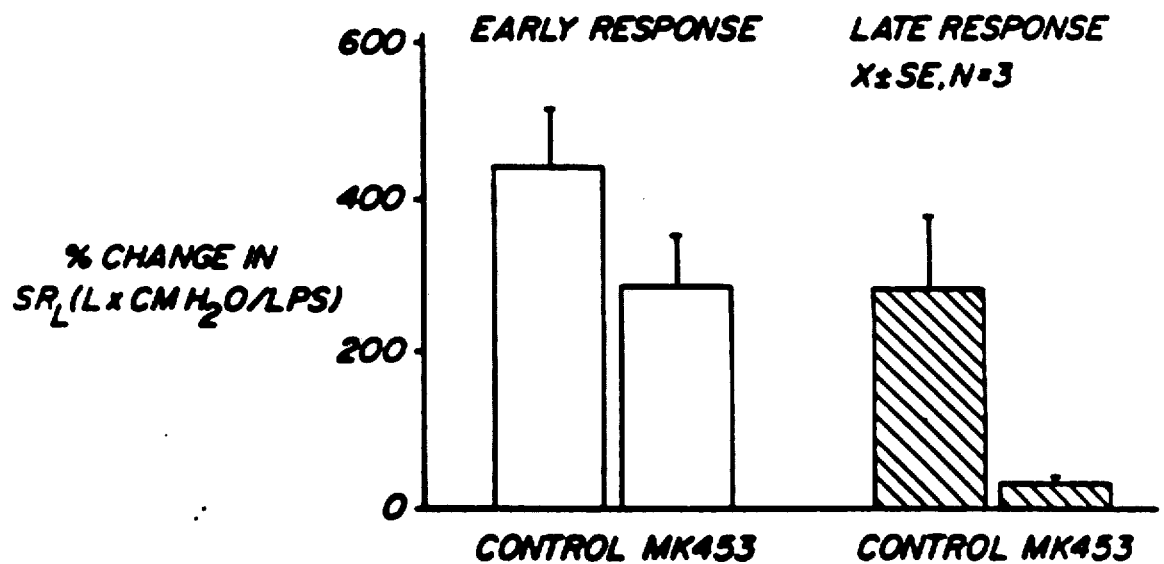
FIG. 1 depicts in bar chart form, the early and late responses of sheep having antigen-induced bronchoconstriction after treatment with (S)-α-fluoromethylhistidine vs. control.

In accordance with the present invention there is provided a method of treating asthma in patients suffering therefrom comprising administering to said patient a therapeutically effective amount of (S)-α-fluoromethylhistidine or a pharmaceutically acceptable salt or ester thereof. There is also provided said method of treatment wherein said therapeutically effective amount is from 10 mg to 2 g per day, preferably 50 mg to 1 g per day.

The present invention further provides a method of reducing or preventing late phase reactions of asthma in patients suffering therefrom comprising administering to said patient a therapeutically effective amount of (S)-α-fluoromethylhistidine or a pharmaceutically acceptable salt or ester thereof. There is also provided said method of treatment wherein said therapeutically effective amount is from 10 mg to 2 g per day, preferably 50 mg to 1 g per day.

In accordance with the present invention it is further provided that for the methods of treatment described above the (S)-α-fluoromethylhistidine is administered as an aerosol.

The present invention still further provides a method of treating asthma in a patient suffering therefrom comprising co-administering to said patient the combination of (a) a therapeutically effective amount of (S)-α-fluoromethylhistidine or a pharmaceutically acceptable salt or ester thereof, and (b) an anti-asthma agent selected from the group consisting of $\beta_2$-agonists, steroids, inhibitors of mediator release, phosphodiesterase inhibitors.

DETAILED DESCRIPTION OF THE INVENTION (S)-α-fluoromethylhistidine and esters thereof may be represented by the following structural formula:

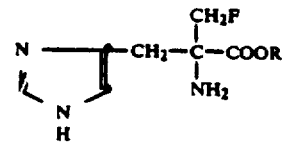

where R is H or a pharmaceutically acceptable ester-forming group. Suitable ester forms will be well-known to, and within the skill of the medicinal chemist. For example, R is preferably $C_{1-4}$ alkyl.

Pharmaceutically acceptable salts of the above compound may also be used in the method of the present invention. These include the acid addition salts of the compound of the formula above as base with a suitable organic or inorganic acid. Preferred inorganic acid salts are hydrohalides, e.g., hydrochlorides, hydroiodides, hydrobromides; the sulfates, and the phosphates. The hydrohalides, and especially the hydrochlorides, are preferred. An especially preferred salt is the hydrochloride hemihydrate salt form, also known as MK-453.

(S)-α-fluoromethylhistidine may be prepared in accordance with methods of synthesis well known in the art. For example, the fluorodehydroxylation method in which the α-hydroxymethylhistidine is treated with SF$_4$ in liquid HF may be used. Details of this method is further described in U.S. Pat. No. 4,325,961.

In the method of treatment of the present invention it is contemplated that the precise unit dosage form and dosage level depend upon the case history of the individual being treated, and that consequently these will be left to the discretion of the therapist. In general, however the (S)-α-fluoromethylhistidine will produce the desired effect of reducing asthmatic symptoms, especially late phase asthmatic symptoms, when given at from about 0.1 to 25 mg/kg of body weight per day. Preferably, this dosage amount will be in the range of from 0.5 to 15 mg/kg. Expressed in other terms, but reflecting the same dosage levels, the amount administered in a single day will be from 10 mg to 2 g. preferably from 50 mg to 1 g per day. Usually, this total daily dosage will be subdivided and given twice a day (b.i.d.), but other dosing regimens may be employed.

The preferred form of delivery, i.e., administration of the (S)-α-fluoromethylhistidine for the treatment of asthma, is in the form of an aerosol, since this form of delivery is best calculated to bring the active agent into direct and most effective contact with the bronchia, where the symptoms of asthma are displayed.

However, it is possible to also employ any of the usual pharmaceutical oral forms well known in the art, such as tablets, elixirs, and aqueous solutions. Thus, e.g., tablets given 1-3 times per day comprising from about 50 mg to about 1 g of (S)-α-fluoromethylhistidine are suitable for human treatment. Sterile solutions for injection comprising from about 50 mg to about 1 g of (S)-α-fluoromethylhistidine given 1-3 times daily are also suitable means of delivery.

It is contemplated that (S)-α-fluoromethylhistidine may be administered alone as the sole therapeutic agent, or that it may be co-administered with any one or more anti-asthma agents, e.g., LTD$_4$ antagonists, PAF antagonists, phosphodiesterase inhibitor, β$_2$-agonists, steroids and inhibitors of mediator release.

Co-administration may mean that the two therapeutic agents are physically combined and given together. But, the term "co-administration" also contemplates that the two therapeutic agents may be given together simultaneously in the same dosage form where the two agents are physically intact and discrete, but are found together in that dosage form.

SHEEP MODEL OF ASTHMA (I.V.)

In this study, carried out in accordance with the protocol of W. M. Abraham, published in W. M. Abraham, Arzneimittelforsching/Drug Research, Vol. 39 (II), No. 10a (1989), pages 1328-1331, 2 iv doses of 30 mg/kg were given at ½ hr before and 4 hrs post antigen challenge. There was little or no reduction of the early response, but the last phase was virtually eliminated. The data are shown in FIG. 1 of the drawings wherein MK-453=(S)-α-Fluoromethylhistidine hydrochloride hemihydrate.

SHEEP MODEL OF ASTHMA (AEROSOL)

Figure 2:
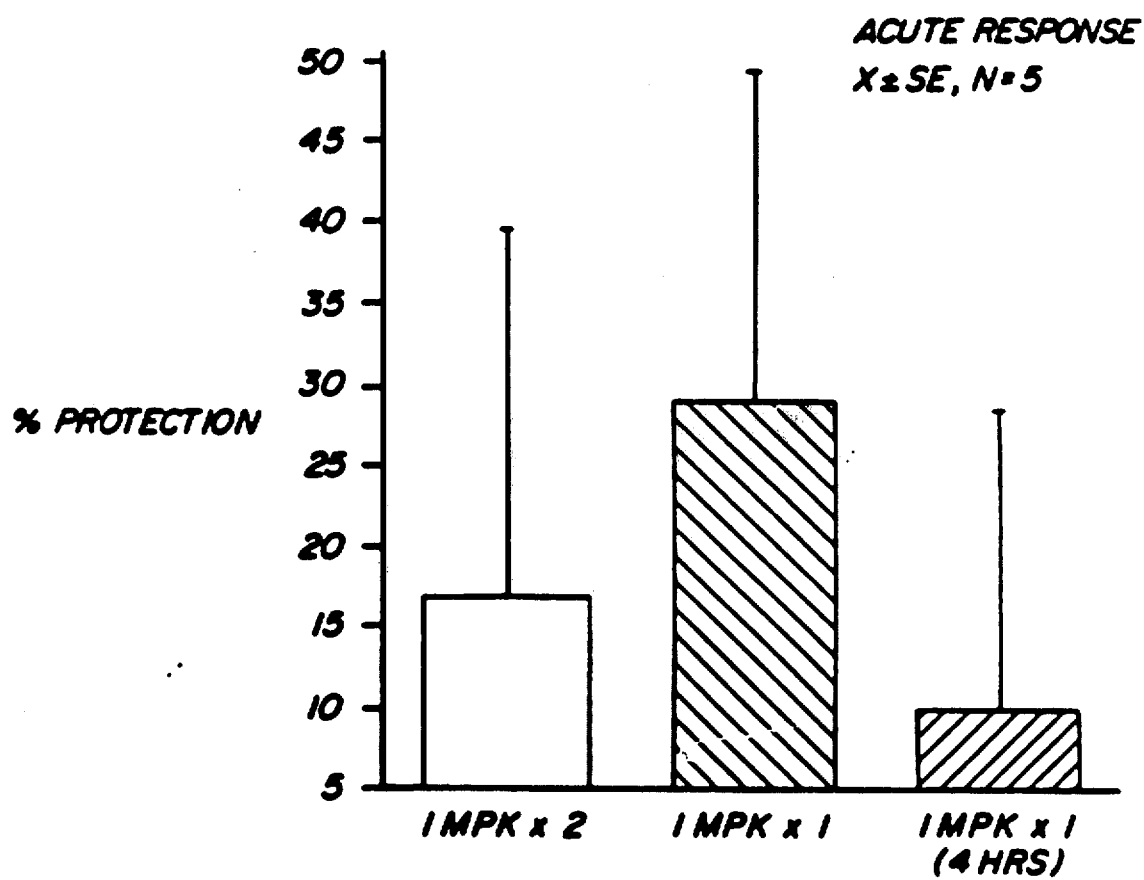
FIGS. 2 and 3 depict in bar chart form the data from a sheep model of asthma in which (S)-α-fluoromethylhistidine vs. control was given as an aerosol at 1 mg/kg at either 30 mins before and 4 hrs after, or as a single dose at 30 mins before antigen challenge, showing that the acute response was not affected but the average late response was eliminated.
Figure 3:
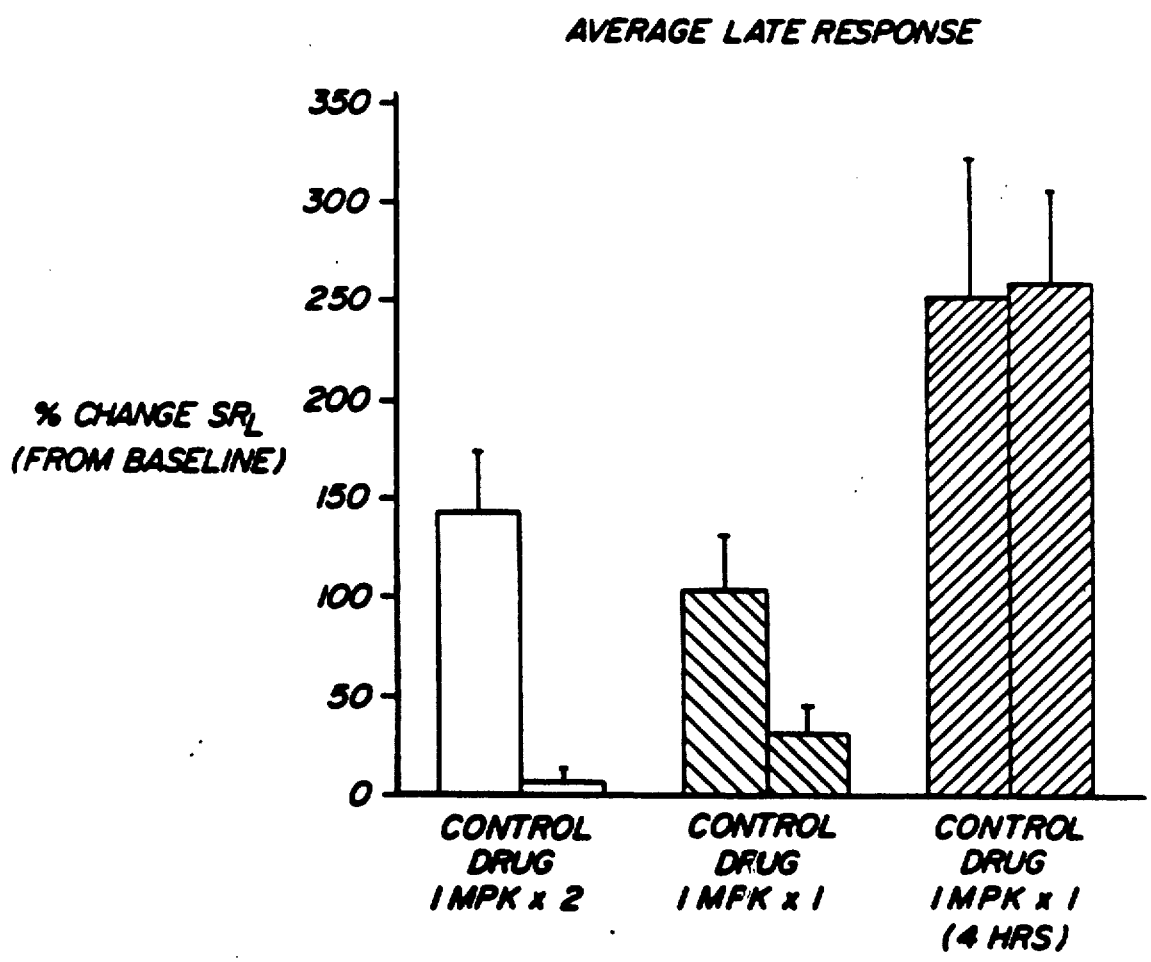

When (S)-α-fluoromethylhistidne was given as an aerosol at 1 mg/kg at either 30 mins before and 4 hrs after, or as a single dose at 30 mins before antigen challenge, the early phase was not affected but the late phase was eliminated. The data are shown in FIGS. 2 and 3 of the drawings.

The aerosol was formed employing a solution prepared by dissolving (S)-α-fluoromethylhistidine hydrochloride hemihydrate (L-641,575=MK-453) in sterile H$_2$O-phosphate buffer at pH 7.3.

What is claimed is:

1. A method of treating asthma in patients suffering therefrom comprising administering to said patient a therapeutically effective amount of (S)-α-fluoromethylhistidine or a pharmaceutically acceptable salt or ester thereof.

2. A method according to claim 1 wherein said therapeutically effective amount is from 10 mg to 2 g per day, preferably 50 mg to 1 g per day.

3. A method reducing or preventing late phase reactions of asthma in patients suffering therefrom comprising administering to said patient a therapeutically effective amount of (S)-α-fluoromethylhistidine or a pharmaceutically acceptable salt or ester thereof.

4. A method according to claim 3 wherein said therapeutically effective amount is from 10 mg to 2 g per day, preferably 50 mg to 1 g per day.

5. A method of treatment according to claim 1 wherein the (S)-α-fluoromethylhistidine is administered as an aerosol.

* * * * *